United States Patent
Vanney et al.

[11] Patent Number: 5,807,405
[45] Date of Patent: Sep. 15, 1998

[54] APPARATUS FOR ATTACHMENT OF HEART VALVE HOLDER TO HEART VALVE PROSTHESIS

[75] Inventors: Guy P. Vanney, Blaine; Kurt D. Krueger, Stacy, both of Minn.

[73] Assignee: St. Jude Medical, Inc., St. Paul, Minn.

[21] Appl. No.: 526,527

[22] Filed: Sep. 11, 1995

[51] Int. Cl.⁶ .................................................. A61F 2/24
[52] U.S. Cl. .......................................... 623/112; 623/900
[58] Field of Search ........................................ 623/2, 900

[56] References Cited

U.S. PATENT DOCUMENTS

| | | | |
|---|---|---|---|
| 3,546,710 | 12/1970 | Shumakov et al. | 3/1 |
| 3,574,865 | 4/1971 | Hamaker | 3/1 |
| 3,828,787 | 8/1974 | Anderson et al. | 128/303 |
| 3,860,005 | 1/1975 | Anderson et al. | 128/303 |
| 4,655,218 | 4/1987 | Kulik et al. | 128/321 |
| 4,683,883 | 8/1987 | Martin | 128/303 |
| 4,755,181 | 7/1988 | Igoe | 623/2 |
| 4,865,600 | 9/1989 | Carpentier et al. | 623/2 |
| 4,932,965 | 6/1990 | Phillips | 623/2 |
| 5,071,431 | 12/1991 | Sauter et al. | 623/2 |
| 5,163,954 | 11/1992 | Curcio et al. | 623/2 |
| 5,236,450 | 8/1993 | Scott | 623/2 |
| 5,370,685 | 12/1994 | Stevens | 623/2 |
| 5,425,705 | 6/1995 | Evard et al. | 604/28 |
| 5,433,700 | 7/1995 | Peters | 604/4 |
| 5,443,502 | 8/1995 | Caudillo | 623/2 |
| 5,578,076 | 11/1996 | Krueger | 623/2 |
| 5,669,919 | 9/1997 | Sanders | 623/2 |

FOREIGN PATENT DOCUMENTS

| | | |
|---|---|---|
| 1690738 A1 | 11/1991 | U.S.S.R. . |
| WO 94/18881 | 9/1994 | WIPO . |
| WO 95/15715 | 6/1995 | WIPO . |
| WO 95/17139 | 6/1995 | WIPO . |

*Primary Examiner*—Michael J. Milano
*Attorney, Agent, or Firm*—Hallie A. Finucane, Esq.; Westman, Champlin & Kelly, P.A.

[57] ABSTRACT

A holder for engaging a heart valve prosthesis during implantation includes a mechanism for attaching the device to the heart valve prosthesis. The heart valve prosthesis includes a circular valve body having an annulus with a substantially annular aperture therein. At least one movable occluder is carried in the aperture and is movable between an open position and a closed position. The attachment mechanism includes a member which couples to the suture cuff thereby affixing the device to the heart valve prosthesis. The attachment mechanism may be actuated to disengage the heart valve prosthesis.

13 Claims, 5 Drawing Sheets

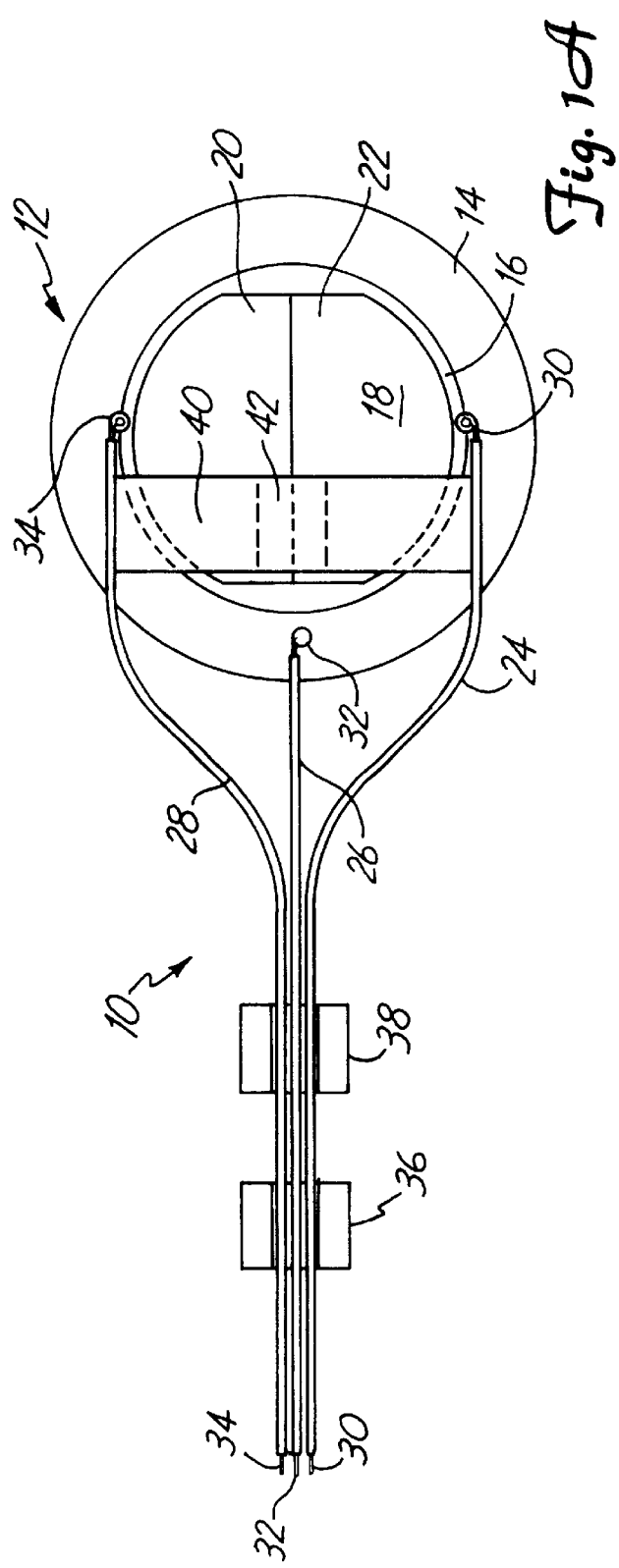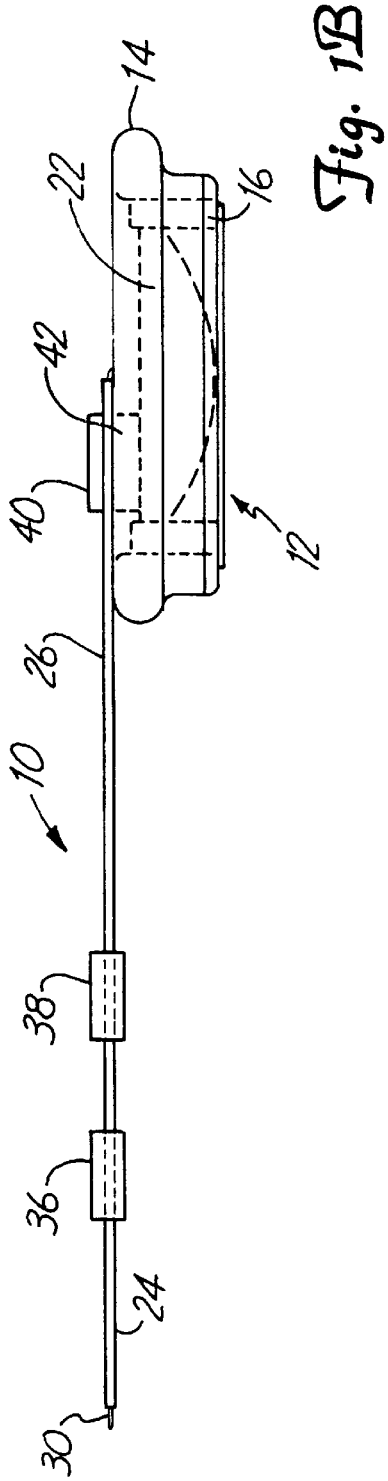

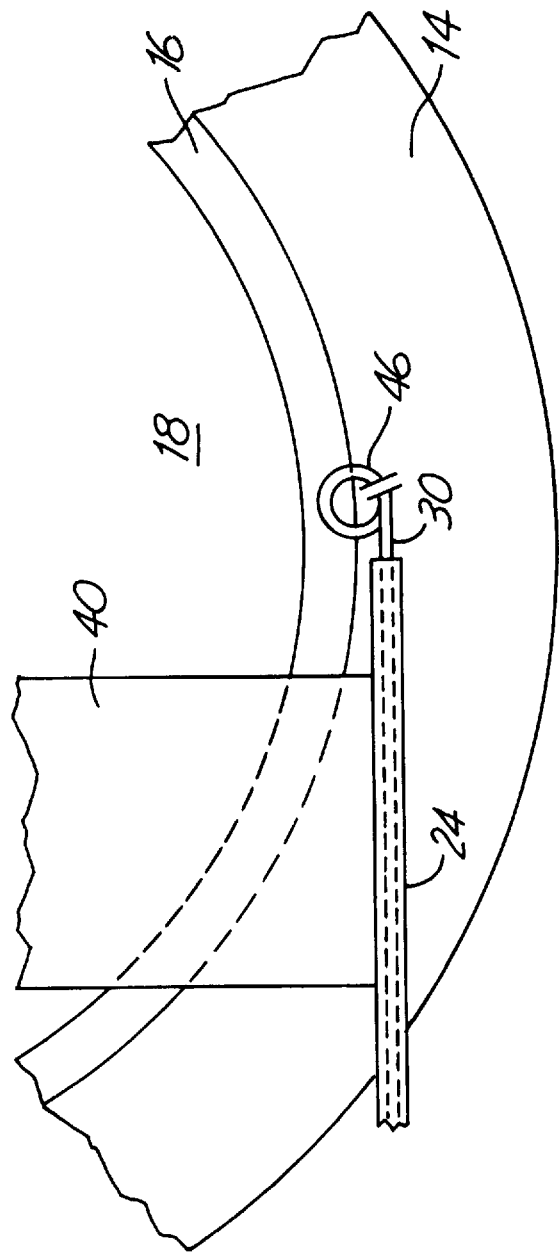

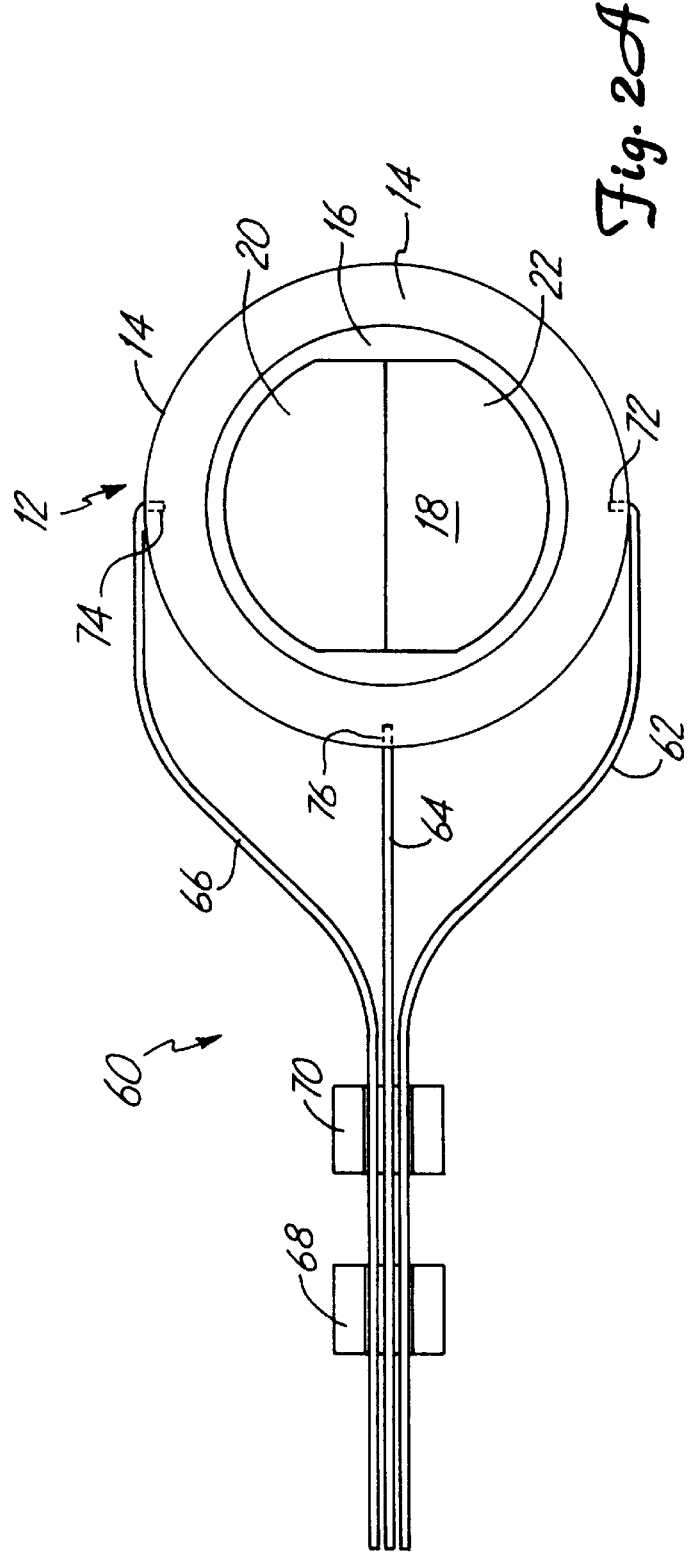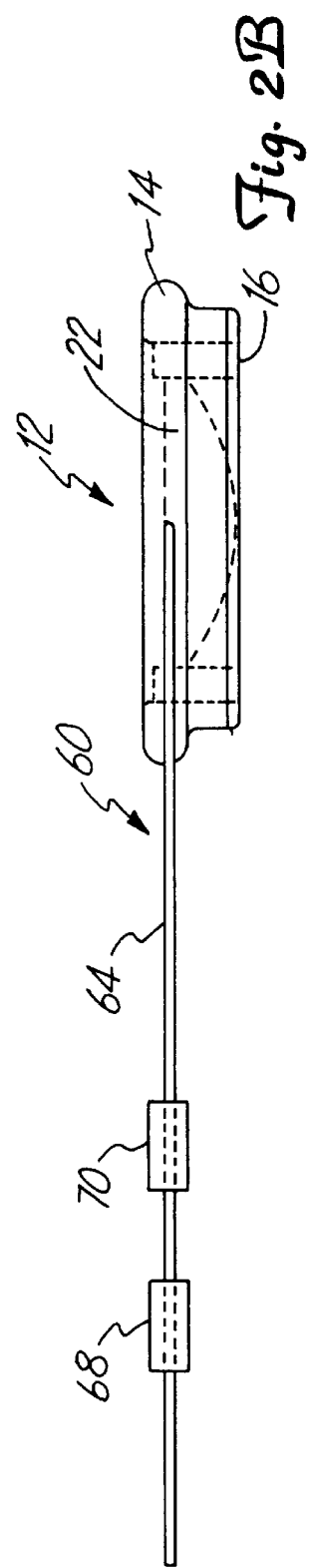

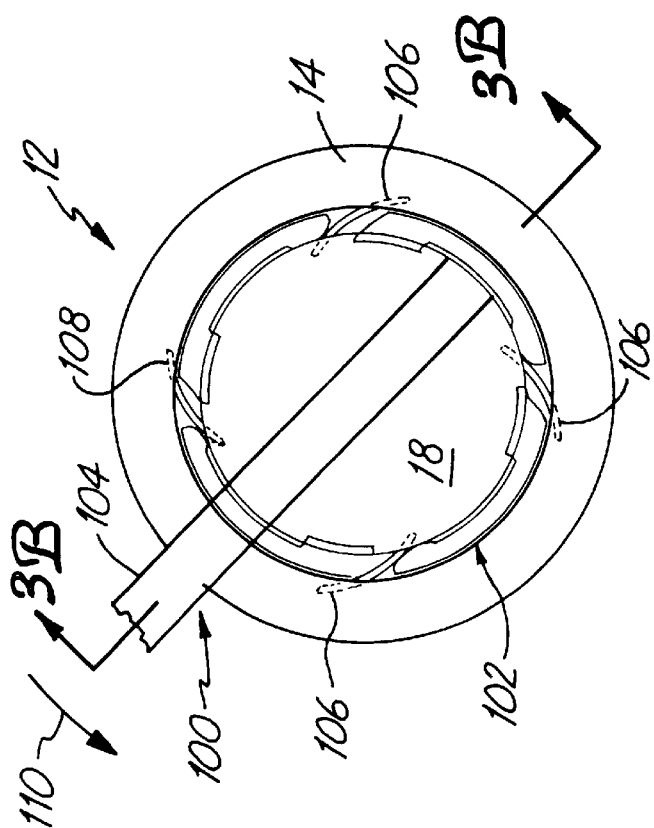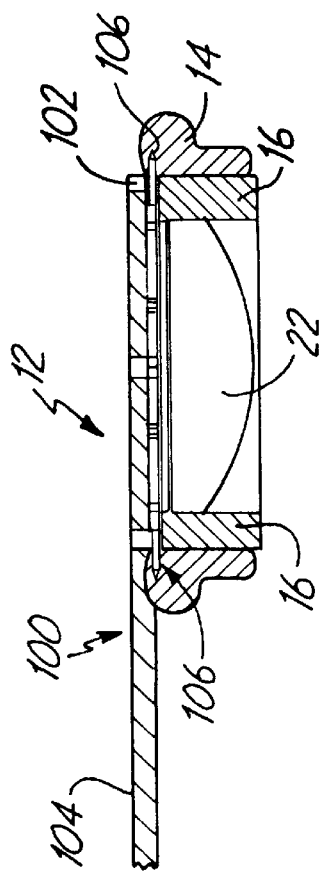

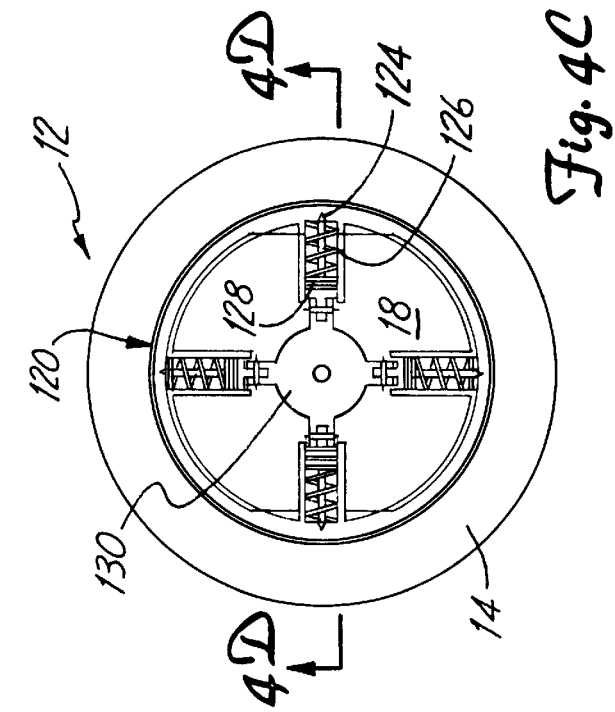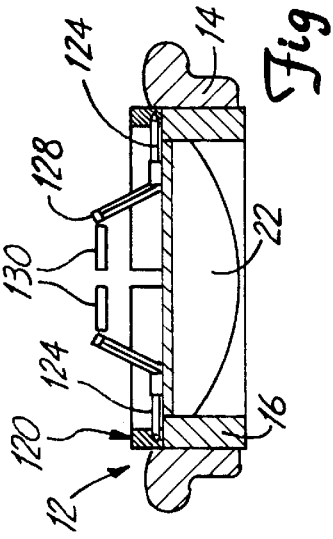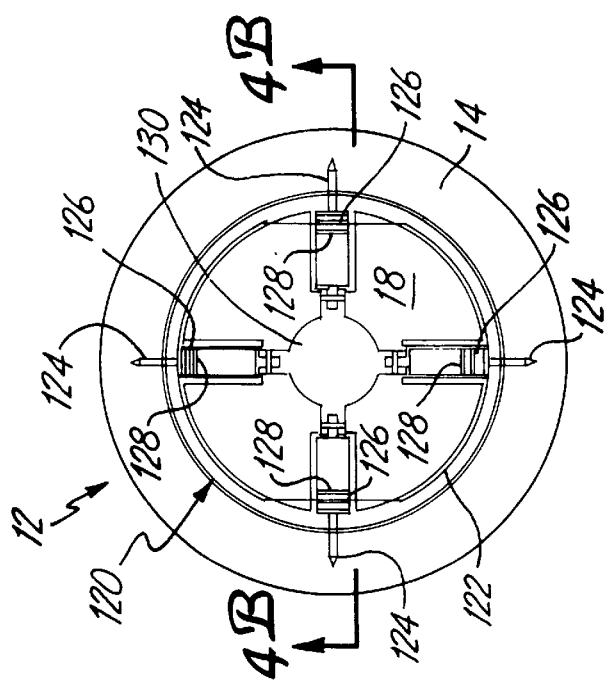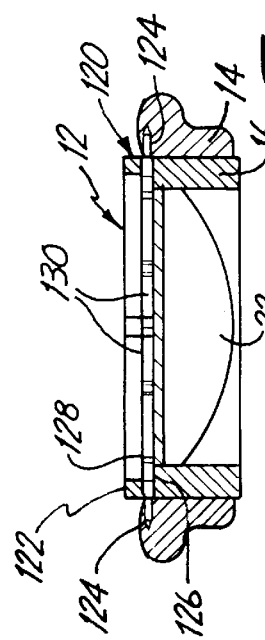

APPARATUS FOR ATTACHMENT OF HEART VALVE HOLDER TO HEART VALVE PROSTHESIS

The present invention relates to devices for implanting heart prostheses. More specifically, the invention relates to attachment of a heart valve holder to a heart valve prosthesis.

BACKGROUND OF THE INVENTION

Holders for holding heart valve prostheses during implantation are known. They are used for positioning, holding, supporting and presenting the valve during surgery. U.S. Pat. No. 3,828,787, issued Aug. 13, 1974, to Anderson et al., entitled COLLET FOR HOLDING HEART VALVE, shows a heart valve holder carried on a distal end of an elongated handle. U.S. Pat. No. 4,932,965, issued Jun. 12, 1990, to Phillips, entitled ARTIFICIAL VALVE, AND NEEDLE AND SUTURE HOLDER AND METHOD OF USING SAME, shows another heart valve holder in which the valve is held against distal ends of a pair of elongated legs during implantation.

Typically, heart valve replacement surgery is an involved procedure in which a sternotomy or thoracotomy is performed and the chest cavity of the patient must be widely opened to provide access to the patient's heart. This provides a surgeon with direct, unobstructed access to the heart. However, this procedure requires a prolonged period to recover from the trauma suffered to the upper torso.

Recently, a procedure has been developed wherein open heart surgery is performed through trocars placed in small incisions between ribs of the patient. This is described in International Publication No. WO 95/15715, entitled DEVICES AND METHODS FOR INTRACARDIAC PROCEDURES; U.S. Pat. No. 5,433,700, issued Jul. 18, 1995, to Peters, entitled METHOD FOR INTRALUMINALLY INDUCING CARDIOPLEGIC ARREST AND CATHETER FOR USE THEREIN; and U.S. Pat. No. 5,425,705, issued Jun. 20, 1995, to Evard et al., entitled THORACOSCOPIC DEVICES AND METHODS FOR ARRESTING THE HEART; and International Publication No. WO 94/18881, entitled METHOD FOR PERFORMING THORACOSCOPIC CARDIAC BYPASS PROCEDURES. In this procedure, elongated tools are used to operate on the heart through the trocars. As discussed in Publication No. WO 95/15715, this procedure can be used during heart valve replacement. When a heart valve prosthesis is inserted through a trocar or similar device, extreme care has to be taken to protect the occluders in the valve, and once inserted, it becomes desirable to change the orientation of the valve prior to implantation to simplify the suturing of the heart valve prosthesis in place.

The trocar results in minimal rib spreading and does not involve the significant chest trauma associated with traditional open heart surgery. One advantage of this procedure is that the recovery period can be reduced significantly. Unfortunately, mechanical heart valves and the associated assembly used for implantation are large relative to the intercostal space between the ribs and are difficult to fit therethrough. Further, the heart valve holder must be securely attached to the heart valve prosthesis and yet be easily removed once the valve has been attached to the heart tissue annulus.

SUMMARY OF THE INVENTION

A device for engaging a heart valve prosthesis during insertion and implantation includes a mechanism for attaching the device to the heart valve prosthesis. The heart valve prosthesis includes a circular valve body having an annulus with a substantially annular aperture therein. At least one movable occluder is carried in the annulus and is movable between an open position and a closed position. The attachment mechanism includes a member which couples to the suture cuff, thereby releasably affixing the device to the valve prosthesis at the suture cuff. The member is selectively removable from the suture cuff, thereby releasing the device from the suture cuff. In one embodiment, an elongated handle couples to the device and extends away from the device in a plane generally parallel with a plane formed by the annulus of the heart valve prosthesis.

In one embodiment, the attachment mechanism is a wire member. This wire member may be looped through the suture cuff or extend substantially directly into the suture cuff.

In one embodiment, the attachment mechanism is disengaged by withdrawing the attachment mechanism from the suture cuff. This may be by directly pulling on the attachment mechanism or by actuating a withdrawal apparatus.

BRIEF DESCRIPTION OF THE DRAWINGS

FIG. 1A is a top plan view of a holder attached to a heart valve prosthesis in accordance with one embodiment.

FIG. 1B is a side view of the holder and prosthesis shown in FIG. 1A.

FIG. 1C is an enlarged plan view showing a portion of the holder of FIG. 1A attached to the heart valve prosthesis.

FIG. 2A is a top plan view of a holder attached to a heart valve prosthesis in accordance with another embodiment.

FIG. 2B is a side plan view of the holder and prosthesis of FIG. 2A.

FIG. 3A is a top plan view showing a holder coupled to a heart valve prosthesis in accordance with another embodiment.

FIG. 3B is a side cross-sectional view of the embodiment of FIG. 3A taken along the line labeled 3B—3B.

FIG. 4A is a top plan view of a holder in accordance with another embodiment of the present invention positioned to engage a heart valve prosthesis.

FIG. 4B is a cross-sectional view of FIG. 4A taken along the line labeled 4B—4B.

FIG. 4C is a top plan view of the holder of FIG. 4A shown in a position to be disengaged from the heart valve prosthesis.

FIG. 4D is a cross-sectional view of FIG. 4C taken along the line labeled 4D—4D.

DETAILED DESCRIPTION OF THE PREFERRED EMBODIMENTS

The invention relates to attachment of a prosthetic heart valve holder to a heart valve prosthesis. The holder is used to position the heart valve prosthesis during implantation. In one embodiment, this implantation is through minimally invasive surgery such as when performed through a small trocar or similar device. The holder and valve are carried at the distal end of a handle which extends perpendicular to the axis of the valve annulus during insertion through the trocar. Reference is made to application Ser. No. 08/526,530 filed on Sep. 11, 1995, now U.S. Pat. No. 5,735,842, entitled LOW PROFILE MANIPULATORS FOR HEART VALVE PROSTHESES. For purposes of this description of the invention, the holder and attachment mechanism will be described generally with regard to its use. The holder and attachment mechanism may be used with any appropriate heart valve prosthesis including heart valve prostheses which are available from St. Jude Medical, Inc., of St. Paul, Minn.; Baxter Healthcare Corp., Edwards CVS Div., Irvine, Calif.; Medtronic, Inc., Minneapolis, Minn.; Shiley, Inc., Irving, Calif.; Omniscience Medical Inc., Grove Heights, Minn.; Carbomedics, Inc., Austin, Tex.; and Sorin Biomedica, Saluggia, Italy. In general, heart valve prostheses depicted herein are shown in a generic form and the scope of the present invention is intended to cover variations required to adapt the holder and attachment mechanism to different heart valve prostheses.

FIG. 1A is a top plan view showing a heart valve holder 10 attached to a heart valve prosthesis 12 in accordance with one embodiment. Prosthesis 12 includes a sewing ring or suture cuff 14 which surrounds heart valve prosthesis body 16. Typically, suture cuff 14 is formed of a soft material suitable for attaching sutures which are used to attach the prosthesis 12 to the valve tissue annulus of a heart. For example, the cuff material may comprise knitted or woven polyester fabric. Heart valve prosthesis body 16 includes an annulus 18 formed therethrough. Occluders 20 and 22 are positioned in annulus 18 and are movable between a closed position, as shown in Figure 1A, and an open position (not shown). Typically these occluders pivot between the open and closed positions. Although the particular heart valve prosthesis 12 has been shown in accordance with one embodiment, other heart valves may also be used with the present invention. For example, the heart valve prosthesis may include different numbers of occluders including a single occluder, may have a different orifice or annulus shape, or the occluder(s) may operate in accordance with a different mechanism.

Holder 10 includes tubes 24, 26 and 28 which have distal ends attached to heart valve prosthesis 12 at cuff 14. Tube 24 carries an elongated wire 30, tube 26 carries elongated wire 32 and tube 28 carries elongated wire 34. Wires 30 through 34 are more flexible then tubes 24 through 28. Tube guides 36 and 38 support tubes 24, 26 and 28. Tubes 24 and 28 are supported at their distal ends by support member 40. Support member 40 spans across annulus 18 of heart valve prosthesis 12.

FIG. 1B is a side view of holder 10 and heart valve prosthesis 12 shown in FIG. 1A. FIG. 1B shows an occluder engagement member 42 which is carried on support member 40. Occluder engagement member 42 engages occluders 20 and 22 to control the movement of the occluders during insertion through the trocar. Occluders 20 and 22 may be maintained in a closed position, an open position, or any position therebetween by the occluder engagement member 42. Orifice 16 provides additional protection to occluders 20 and 22 if the occluders are maintained in the closed position. Occluder engagement member 42 is preferably made of a material which will not damage occluders 20 and 22, for example a soft malleable material such as sponge material.

FIG. 1C is a detailed plan view taken from FIG. 1A showing attachment of wire 30 to suture cuff 14 of heart valve prosthesis 12. Wire 30 is formed in a loop or pigtail 46 which extends into the material of cuff 14. This is one preferred embodiment. In other embodiments, wire 30 may extend further into cuff 14 and may even circumscribe the entire radius of cuff 14.

In operation, heart valve 12 is inserted into the annulus which remains after the patient' native valve has been surgically excised, hereinafter referred to as tissue annulus.

The surgeon controls positioning of the valve 12 by manipulating the proximal end of tubes 24, 26 and 28. During insertion, the surgeon can pivot the valve about the distal ends of wires 30 and 34 by selectively pushing or pulling tube 26. For example, valve 12 can be maintained in a position similar to FIG. 1B such that the plane of the valve is parallel with elongated tubes 24, 26 and 28 during insertion through a trocar sleeve or similar opening and then manipulate or rotate the valve for insertion into the heart tissue annulus following insertion through the trocar by pushing on tube 26 and pulling on tubes 24 and 28. Following placement and attachment of valve 12 to the heart tissue annulus, holder 10 may be removed by pulling on wires 30, 32 and 34 which protrude from the proximal ends of tubes 24, 26 and 28 respectively, thereby drawing wires 30, 32 and 34 into the tubes 24, 26 and 28. The wires 30, 32 and 34 are straightened when drawn into tubes 24, 26 and 28 and the holder 10 is released from cuff 14. For example, coil 46 unwinds and is released from cuff 14. Support member 40 and tubes 24, 26 and 28 are of a rigid and biocompatible material, such as stainless steel or polysulfone. Variations on this embodiment include different techniques for attaching wires to cuff 14. However, the attachment to cuff 14 needs to be releasable such that the holder may be removed following insertion of heart valve prosthesis 12. Suitable materials for the wire member include metal, polymers or other appropriate biocompatible material such as polytetrafluoroethylene (PTFE) or acetal. The wire member should be of a material which can transmit a pulling or pushing force from the proximal end of handle 10 to the distal end. This is unlike a typical prior art suture which was used to attach a heart valve to a holder.

FIG. 2A is a top perspective view and FIG. 2B is a side plan view showing a holder 60 attached to heart valve prosthesis 12 in accordance with another embodiment. Holder 60 includes elongated members 62, 64 and 66 which releasably couple to suture cuff 14. Members 62, 64 and 66 are held by support members 68 and 70. Members 62 and 66 include tip portions 72 and 74 adapted for grasping suture cuff 14. A tip portion 76 of member 64 is also adapted for engaging cuff 14. In the embodiment shown in FIGS. 2A and 2B, tip portions 72, 74 and 76 extend into cuff 14 thereby securing holder 60 to cuff 14. Tip portion 76 of member 64 acts to stabilize cuff 14 to control rotation of cuff 14 about tip members 72 and 74. In a manner similar to that described for holder 10 shown FIGS. 1A through 1C, heart valve prosthesis 12 may be rotated or manipulated by a surgeon urging member 64 in a direction toward the distal end of holder 60. This motion causes valve 12 to be manipulated after insertion into the patient and thereafter attached to the heart tissue annulus. Following attachment of valve 12 to the patient's heart annulus, holder 60 is withdrawn from valve 12 by spreading members 62 and 66 apart causing tip members 72 and 74 to separate from valve 12. Spreading should be sufficient to free valve 12. Holder 60 may then be removed from the patient.

FIG. 3A shows a holder 100 coupled to heart valve prosthesis 12 in accordance with another embodiment. Holder 100 includes body portion 102 and elongated handle 104. Body 102 includes protruding attachment members 106. FIG. 3B is a side cross-sectional view of the embodiment of FIG. 3A taken along the line labeled 3B—3B. Holder 100 is secured to valve 12 by members 106 which enter and grasp cuff 14. This secures body 102 against heart valve prosthesis body 16.

During implantation, a surgeon manipulates valve 12 using elongated handle 104 to insert and position valve 12 adjacent the tissue annulus of the patient's heart. Following attachment of valve 12 to the patient's heart, holder 100 is disengaged from valve 12 by turning holder 100 in a direction as shown by arrow 110 in FIG. 3A. Variations on this embodiment are also within the scope of the present invention. For example, members 106 may be actuated by an actuation member such as a cam or other member causing members 106 to retract from cuff 14 in an inwardly direction toward the center of annulus 18.

FIG. 4A is a top plan view showing a holder 120 in accordance with another embodiment coupled to heart valve prosthesis 12. FIG. 4B is a cross-sectional view of FIG. 4A taken along line 4B—4B. FIGS. 4A and 4B show holder 120 engaged with cuff 14. Holder 120 includes holder body 122 positioned in abutting contact with heart valve prosthesis body 16. Holder 120 includes engaging members 124 which extend into cuff 14. A spring 126 is compressed between an outer circumference of body 122 and an inner edge 128 of engaging members 124. An elongated handle (not shown in FIGS. 4A through 4D) extends in a direction parallel with the plane of holder body 122 and is used by a surgeon during insertion of heart valve prosthesis 12. Following attachment of valve 12 to the tissue annulus, holder 120 may be removed by disengaging members 124 from suture cuff 14, as shown in FIGS. 4C and 4D. By providing a lifting force to central member 130, springs 126 are able to expand thereby withdrawing members 124 from cuff 14. Actuation of holder 120 to allow withdrawal may be through any mechanism such as, for example, applying a lifting force or removing a lock member. As used herein, attachment mechanism is used to mean a mechanism for attaching to the suture cuff. The preferred embodiments set forth a number of attachment mechanisms. However, the term "attachment mechanism" is intended to describe any other mechanism for attaching a valve to a cuff which is within the scope of the invention.

It should be understood that the present invention extends to any variation or embodiment which would be apparent to those skilled in the art. The concepts set forth herein are applicable to any appropriate valve configuration for both aortic and mitral implantation. Further, the suture cuff may be positioned in other appropriate locations in the heart valve prosthesis so long as it is accessible to engagement mechanisms and techniques within the scope of the invention. An occluder engagement member may be included in any of the embodiments to control the occluders during implantation. Typically, the occluder is maintained in a partially closed position to protect the occluder during implantation.

Although the present invention has been described with reference to preferred embodiments, workers skilled in the art will recognize that changes may be made in form and detail without departing from the spirit and scope of the invention.

What is claimed is:

1. An apparatus for holding a heart valve prosthesis during implantation, the heart valve prosthesis including a heart valve prosthesis body, a movable occluder and a suture cuff, the apparatus comprising:

a body adapted for abutting the heart valve prosthesis;

a bendably rigid tip member having a proximal end and a free distal end coupled to the body and adapted to detachably engage the suture cuff by extending into the suture cuff, whereby the free distal end may be selectively detached from the suture cuff by movement of the proximal end; and an elongated handle having a distal end coupled to the body.

2. The apparatus of claim 1 wherein the prosthesis has an annulus and the handle is adapted to extend in a direction generally parallel with a plane defined by the annulus when the heart valve is positioned adjacent the body.

3. The apparatus of claim 1 wherein the tip member comprises a bendable coil which is adapted to be removably coiled into the suture cuff to secure the heart valve to the apparatus.

4. The apparatus of claim 1 wherein the tip member further comprises a second free distal end coupled to the body and adapted to detachably engage the suture cuff.

5. The apparatus of claim 4 wherein the free distal ends of the tip member are adapted to engage the suture cuff at approximately opposite sides of the suture cuff forming a pivot therebetween.

6. The apparatus of claim 5 wherein the tip member further comprises a third free distal end adapted to engage the suture cuff at a location between the first and second distal ends.

7. The apparatus of claim 6 wherein the third distal end is adapted for movement along an axis of the elongated handle thereby translating a force along the axis adapted to cause the prosthesis to rotate about the pivot.

8. The apparatus of claim 1 wherein the suture cuff forms an annulus and the distal end of the tip member is adapted to extend in an angular direction into the suture cuff when the heart valve is coupled to the apparatus.

9. The apparatus of claim 8 including a plurality of free distal ends which can extend at an angular direction into the suture cuff and be selectively removable from the cuff by movement in a reverse angular direction.

10. The apparatus of claim 1 wherein the suture cuff is annular and the free distal end of the tip member can extend in a radially outward direction into the suture cuff.

11. The apparatus of claim 10 including a plurality of free distal ends which can extend in radially outward directions into the suture cuff, the plurality of free distal ends being selectively removable from the suture cuff by movement in a radially inward direction.

12. The apparatus of claim 11 including an actuating mechanism coupled to the plurality of free distal ends providing the radially inward movement to selectively remove the distal ends of the tip member.

13. The apparatus of claim 12 wherein the actuating mechanism includes a spring.

* * * * *